US006329536B1

(12) United States Patent
Ji et al.

(10) Patent No.: US 6,329,536 B1
(45) Date of Patent: Dec. 11, 2001

(54) STEREOSELECTIVE PROCESS FOR PRODUCING NITRO COMPOUNDS

(75) Inventors: Jianguo Ji, Libertyville; David M. Barnes, Lake Villa; Steve King, Gurnee, all of IL (US); Frederick A. Plagge, Port Washington, WI (US); Steven J. Wittenberger, Mundelein; Ji Zhang, Gurnee, both of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/397,538

(22) Filed: Sep. 16, 1999

Related U.S. Application Data

(63) Continuation-in-part of application No. 09/152,844, filed on Sep. 14, 1998, now abandoned.

(51) Int. Cl.$^7$ ...................... C07C 205/02; C07D 317/64
(52) U.S. Cl. ............................. 549/444; 568/307
(58) Field of Search .................................. 548/217, 224, 548/239, 526; 549/444; 568/307

(56) References Cited

PUBLICATIONS

Bako, P., et al., "Asymmetric C–C Bond Forming Reactions by Chiral Crown Catalysts; Darzens Condensation and Nitroalkane Addition to the Double Bond", *Synlett*, 291–292 (1997).

Bako, P., et al., "Chiral Azacrown Ethers Derived from D–glucose as Catalysts for Enantioselective Michael Addition", *Tetrahedron Letters*, 38(41):7259–7262 (1997).

Davies, I.W., et al., "Application of Indane–derived C2–Symmetric Bis(oxazolines) in Two–point Binding Asymmetric Diels–Alder Reactions", *Tetrahedron Letters*, 37(11):1725–1726 (1996).

Davies, I.W., et al., "A Conformational Toolbox of Oxazoline Ligands", *Tetrahedron Letters*, 38(7):1145–1148 (1997).

Mulzer, J., et al., "Enantioselective Synthesis of the Antidepressant Rolpram by Michael Addition to a Nitroolefin", *Angew. Chem. Int. Ed. Engl.*, 31(7):870–872 (1992).

Sasai, H., et al., "Catalytic Asymmetric Michael Reactions Promoted by a Lithium–Free Lanthanum–BINOL Complex", *American Chemical Society*, 116:1571–1572 (1994).

Sasai H., et al., "Catalytic Asymmetric Michael Reactions Promoted by the La–Na–BINOL Complex (LSB). Enantioface Selection on Michael Donors", *Tetrahedron Letters*, 37(31):5561–5564 (1996).

Sasai M.P., et al., "Chiral Lewis Acid Catalysis in Conjugate Additions of O–Benzylhydroxylamine to unsaturated Amides. Enantioselective Synthesis of β–Amino Acid Precursors", *J. Am. Chem. Soc.*, 120:6615–6616 (1998).

Sibi, M.P. & Ji, J., "Practical and Efficient Enantioselective Conjugate Radical Additions", *J. Org. Chem.*, 62:3800–3801 (1997).

Yamaguchi, M., et al., "A Catalytic Enantioselective Michael Addition of a Simple Malonate to Prochiral x, β–Unsaturated Ketones and Aldehydes", *Angew. Chem. Int. Ed. Engl.*, 32(8):1176–1178, 1993.

Bernardi, A., et al., "Enantioselective Mukaiyama–Michael Reactions of 2–Carbomethoxy cyclopentenone Catalyzed by Chiral Bis(Oxazoline)–Cu(II) Complexes", *Tetrahedron Letters*, 37(49):8921–8924 (1996).

Brimble, M. A., et al., "Use of bis(oxazoline)–metal complexes as chiral catalysts for asymmetric Diels–Alder reactions using 2–acetyl–1,4–naphthoquinone as a dienophile", *Tetrahedron:Asymmetry*, 8(24):4069–4078 (1997).

Brunner, H., et al., Asymmetric Catalysis, CIII[1]: Enantioselective Michael Addition of 1,3–Dicarbonyl Compounds to Conjugated Nitroalkenes, *Monatshefte for Chernie*, 127:1063–1072 (1996.

Ghosh, A. K., et al., "C2–Symmetric chiral bis(oxazoline)–metal complexes in catalytic asymmetric synthesis", *Tetrahedron:Asymmetry*, 9(32):1–45 (1998).

Ji, J., et al., "Catalytic Enantioselective Conjugate Addition of 1,3–Dicarbonyl Compounds to Nitroalkenes", *J. Am. Chem. Soc.*, 121:10215–10216 (1999).

*Primary Examiner*—Taofiq A. Solola
(74) *Attorney, Agent, or Firm*—B. Gregory Donner; Michael J. Ward

(57) ABSTRACT

The present invention relates to producing stereoselective nitro compounds by reacting a dicarbonyl compound with a nitrostyrene compound in the presence of a catalyst complex and a base.

12 Claims, No Drawings

STEREOSELECTIVE PROCESS FOR PRODUCING NITRO COMPOUNDS

This application is a continuation-in-part of U.S. application Ser. No. 09/152,844, filed Sep. 14, 1998, incorporated herein by reference now abandoned.

BACKGROUND OF THE INVENTION

The addition reactions of a beta-dicarbonyl compounds such as IV to nitroolefins such as III can proceed to give either of two enantiomers, Va or Vb of the insipient nitromethyl group. No methods currently exist to select for the formation of Va or Vb via the action of a catalyst.

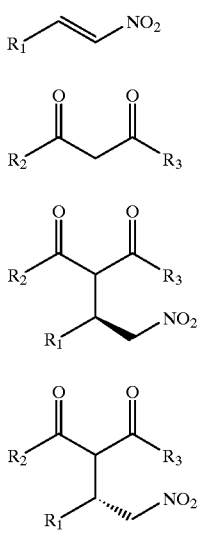

SUMMARY OF THE PRESENT INVENTION

The present invention provides a process for enantioselectively producing a nitromethyl compound having formula Va or Vb from a nitroolefin having formula III and a beta dicarbonyl compound having formula IV wherein, $R_1$=aryl, alkyl or arylalkyl, and $R_2$ and $R_3$ are independently selected from alkoxy, alkyl, arylalkyl, and or aryl, in the presence of a catalyst complex and a base, said catalyst complex comprising a ligand and a metal complex, wherein the ligand has the formula I

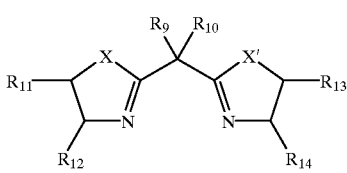

wherein
  $R_9$ and $R_{10}$ are independently selected from the group consisting of hydrogen, alkyl, aryl, and arylalkyl, or $R_9$ and $R_{10}$ taken together can form a 3, 4, 5, or 6-membered cycloalkyl ring or a bicyclic ring;
  X and X' are independently selected from the group consisting of oxygen, sulfur, and nitrogen;
  $R_{11}$ or $R_{12}$ may be independently selected from the group consisting of hydrogen, alkyl, arylalkyl, and aryl, or $R_{11}$ and $R_{12}$ taken together with the ring to which they are attached may form a bicyclic or tricyclic fused ring; and $R_{13}$ or $R_{14}$ may be independently selected from the group consisting of hydrogen, alkyl, arylalkyl, and aryl, or $R_{13}$ and $R_{14}$ taken together with the ring to which they are attached may form a bicyclic or tricyclic fused ring; or the ligand can have the formula II,

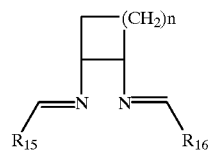

wherein n is 1–3, and $R_{15}$ and $R_{16}$ are independently selected from the group consisting of alkyl, aryl, and arylalkyl.

DETAILED DESCRIPTION OF THE PRESENT INVENTION

The present invention provides a process for enantioselectively producing a nitromethyl compound from a nitroolefin having formula III and a beta dicarbonyl compound having formula IV wherein, $R_1$=aryl, alkyl or arylalkyl, $R_2$ and $R_3$ are independently selected from alkoxy, alkyl, arylalkyl, or aryl, in the presence of a catalyst complex and a base, said catalyst complex comprising a ligand and a metal complex, wherein the ligand has the formula I

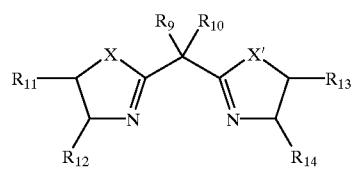

wherein
  $R_9$ and $R_{10}$ are independently selected from the group consisting of hydrogen, alkyl, aryl, and arylalkyl, or $R_9$ and $R_{10}$ taken together can form a 3, 4, 5, or 6-membered cycloalkyl ring or a bicyclic ring;
  X and X' are independently selected from the group consisting of oxygen, sulfur, and nitrogen;
  $R_{11}$ or $R_{12}$ may be independently selected from the group consisting of hydrogen, alkyl, arylalkyl, and aryl, or $R_{11}$ and $R_{12}$ taken together with the ring to which they are attached may form a bicyclic or tricyclic fused ring; and $R_{13}$ or $R_{14}$ may be independently selected from the group consisting of hydrogen, alkyl, arylalkyl, and aryl, or $R_{13}$ and $R_{14}$ taken together with the ring to which they are attached may form a bicyclic or tricyclic fused ring; or the ligand can have the formula II,

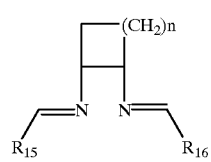

wherein n is 1–3, and $R_{15}$ and $R_{16}$ are independently selected from the group consisting of alkyl, aryl, and arylalkyl.

A more preferred embodiment of the present invention provides for a Michael addition of a nitrostyrene compound and a ketoester substrate in the presence of a base and a catalyst complex to provide a stereoselective nitro compound.

Another preferred embodiment of the present invention provides for a Michael addition of a nitrostyrene compound and a ketoester substrate in the presence of a base and a catalyst complex to provide a nitro compound.

Another preferred embodiment of the present invention relates to a process of producing 2-arylnitroethane derivatives by reacting an arylnitrostyrene compound with a 1,3 dicarbonyl substrate in the presence of a base and a catalyst complex.

Another preferred embodiment of the present invention relates to a process of reacting a a nitroolefin having formula III and a beta dicarbonyl compound having formula IV wherein R1 is aryl, R2 is aryl or all, and R3 is alkoxy.

Another preferred embodiment of the present invention relates to a process of reacting a a nitroolefin having formula III and a beta dicarbonyl compound having formula IV wherein R1 is substituted 3,4-dioxanylphenyl, R2 is aryl or alkyl, and R3 is alkoxy. The processes and intermediates contained herein are useful in the production of pharmaceuticals, particularly endothelin antagonists. In particular, the processes and intermediates contained herein are useful in synthesizing endothelin antagonists having a pyrrolidine core and obtaining high optical purity.

For purposes of the disclosure, the following terms are defined herein.

The terms "loweralkyl" or "alkyl" as used herein refer to straight or branched chain alkyl radicals containing from 1 to 6 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "alkoxy" as used herein refers to $R_{41}O-$ wherein $R_{41}$ is a loweralkyl group, as defined above. Examples of alkoxy include, but are not limited to, ethoxy, tertbutoxy, and the like.

The term "aryl" as used herein refers to a mono- or bicyclic carbocyclic ring system having one or more aromatic rings including, but not limited to, phenyl, naphthyl, tetrahydronaphthyl, naphthyridinyl, indanyl, indenyl and the like. Aryl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide. In addition, substituted aryl groups include tetrafluorophenyl and pentafluorophenyl.

The term "arylalkyl" as used herein refers to an aryl group as previously defined, appended to a loweralkyl radical, for example, benzyl and the like.

The term "cycloalkyl" as used herein refers to an aliphatic ring system having 3 to 10 carbon atoms and 1 to 3 rings including, but not limited to, cyclopropyl, cyclopentyl, cyclohexyl, norbornyl, adamantyl, and the like. Cycloalkyl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

The catalyst complex is formed by reacting a ligand and a metal complex together. The ligand and the metal complex may be reacted together in the presence of a solvent. The time necessary for the catalyst complex to form can vary for the particular ligand and metal complex used. For example, a particular ligand and metal complex may need only 30 minutes or as much as several hours depending on the reactants used. Alternatively, one skilled in the art may add the base, nitroolefin and dicarbonyl compounds simultaneously to the ligand, metal complex and solvent. Solvents suitable for the formation of the catalyst complex include but are not intended to be limited to, tetrahydrofuran (THF), toluene, methylene chloride, and chloroform. The preferred solvent is chloroform.

Ligands suitable for the present invention have the formula I

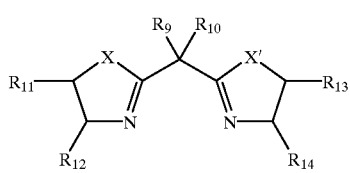

I wherein

R9 and R10 are independently selected from the group consisting of hydrogen, aryl, and arylalkyl, or R9 and R10 taken together can form a 3, 4, 5, or 6-membered cycloalkyl ring or a bicyclic ring;

X and X' are independently selected from the group consisting of oxygen, sulfur, and nitrogen;

R11 or R12 may be independently selected from the group consisting of hydrogen, alkyl, arylalkyl, and aryl, or R11 and R12 taken together with the ring to which they are attached may form a bicyclic or tricyclic fused ring;

R13 or R14 may be independently selected from the group consisting of hydrogen, alkyl, arylalkyl, and aryl, or R13 and R14 taken together with the ring to which they are attached may form a bicyclic or tricyclic fused ring; or the ligand can have the formula II,

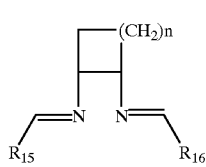

II wherein n is 0–3, and R15 and R16 are independently selected from the group consisting of alkyl, aryl, and arylalkyl.

More preferred ligands of the present invention have formula VI or VII are

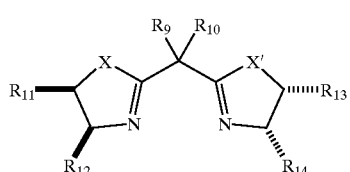

VI

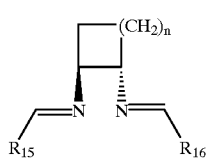

VII wherein R9, R10, X, X', R11, R12, R13, R14, n, R15 and R16 are as defined above, and Formula VI and VII's enantiomers.

A more preferred embodiment of the present invention utilizes a ligand of formula I having the following structure

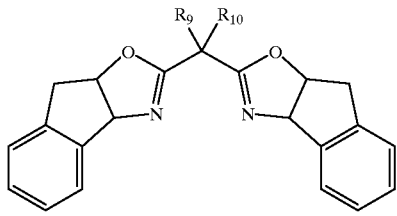

wherein R9 and R10 are independently selected from methyl, ethyl, propyl, and isopropyl, and arylalkyl, or R9 and R10 taken together form cyclopropyl, cyclobutyl, cyclopentyl, or indanyl.

Another preferred embodiment of the present invention utilizes a ligand of formula VI having the following structure

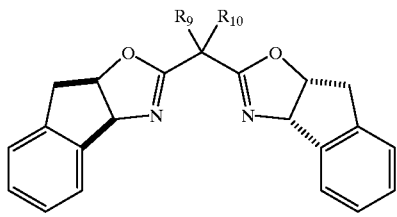

wherein R9 and R10 are independently selected from methyl, ethyl, propyl, and isopropyl, and arylalkyl, or R9 and R10 taken together form cyclopropyl, cyclobutyl, cyclopentyl, or indanyl, and its enantiomer.

Another preferred embodiment of the present invention utilizes a ligand of formula I and VI having the structure

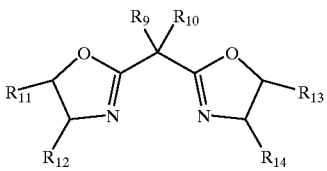

wherein wherein R9 and R10 are independently selected from methyl, ethyl, propyl, and isopropyl, and arylalkyl, or R9 and R10 taken together form cyclopropyl, cyclobutyl, cyclopentyl, or indanyl, and R11, R12, R13, and R14 are independently selected from the group consisting of hydrogen, alkyl, aryl, and arylalkyl.

Another preferred embodiment of the present invention utilizes a ligand of formula I and IV

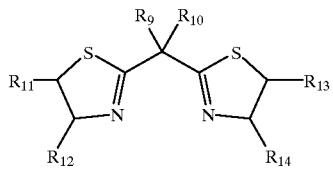

wherein R9 and R10 are independently selected from methyl, ethyl, propyl, and isopropyl, and arylalkyl, or R9 and R10 taken together form cyclopropyl, cyclobutyl, cyclopentyl, or indanyl, and R11, R12, R13, and R14 are independently selected from the group consisting of hydrogen, alkyl, aryl, and arylalkyl.

Metal complexes suitable for providing a catalyst complex include, but are not intended to be limited to, magnesium trifluoromethanesulfonate, magnesium perchlorate, copper trifluoromethanesulfonate, zinc trifluoromethanesulfonate, lanthanum trifluoromethanesulfonate, nickel trifluoromethanesulfonate, magnesium bromide, copper bromide, zinc bromide, nickel bromide, magnesium iodide, copper iodide, zinc iodide, nickel iodide, magnesium acetylacetonate, copper acetylacetonate, zinc acetylacetonate, and nickel acetylacetonate. The more preferred metal complex is magnesium trifluoromethanesulfonate.

Bases suitable for the present invention include, but are not intended to be limited to, triethylamine, diisopropyl ethylamine, 2,6-lutidine, N-methylmorpholine, N-ethylpiperidine, imidazole, and 5,6-dimethylbenzimidazole. The more preferred bases are 2,6-lutidine, N-methylmorpholine , and 5,6-dimethylbenzimidazole.

EXAMPLE 1

Ligand Synthesis

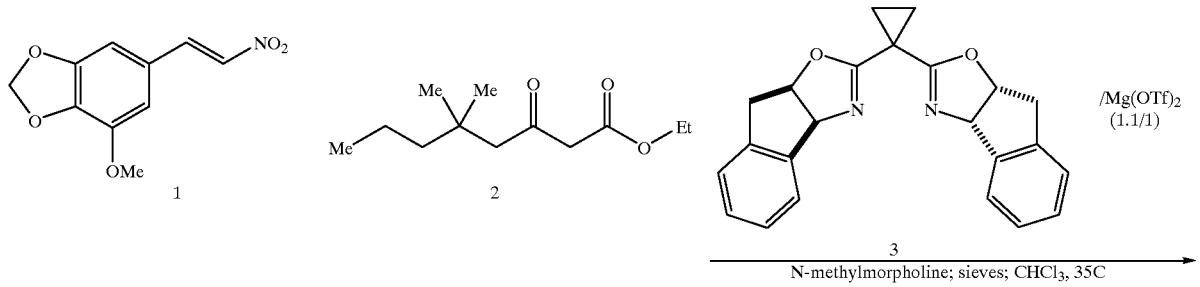

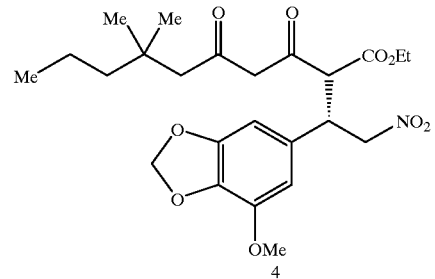

4

Bis(oxazoline) 2. A 3-neck, IL round bottom flask was charged with diethyl malonimidate dihydrochloride (Aldrich; 46.22 g; 0.20 Mol; 1.0 equiv.) and 250 mL of THF was added. The reaction vessel was fitted with an overhead stirrer, and a thermometer. Aminoindanol (Aldrich; 29.84 g; 0.20 Mol; 1.0 equiv.) was added, a condenser was added, and the reaction was heated to reflux. After 5 hours, the heat was removed. After cooling to room temperature, the reaction was transferred to a 2L, 3-neck round bottom flask equipped with a thermometer, a mechanical stirrer and an addition funnel. The reaction was cooled in an ice-water bath to ~5° C. Aqueous NaHCO₃ (0.5 N; 1.2 L; 0.60 mmol) was added at a rate such that the reaction temperature remained below 15° C. Further cooling brought the temperature to below 5° C. An aliquot of the supernatant was filtered.

The product was collected by filtration through a fritted funnel, and the filter cake was washed twice with 200 mL of water. The product was dried overnight at room temperature under vacuum with a nitrogen bleed. The product weighed 28.76 g, which was analyzed to contain 28.62 g (99.5% pure; 87% yield) of bis(oxazoline) 2.

2: $^1$H NMR (300 MHz/CDCl₃) δ7.39 (m, 2H, Ar—H); 7.22–7.15 (m, 6H, Ar—H); 5.50 (d, J=7.8 Hz, 2H, N—CH); 5.27 (m, 2H, O—CH); 3.32 (dd, J=7.0, 18.0 Hz, 2H, Ar—CHH); 3.20 (m, 2H, C₂—H₂); 3.09 (dd, J=1.5, 18.0 Hz, 2H, Ar—CHH).

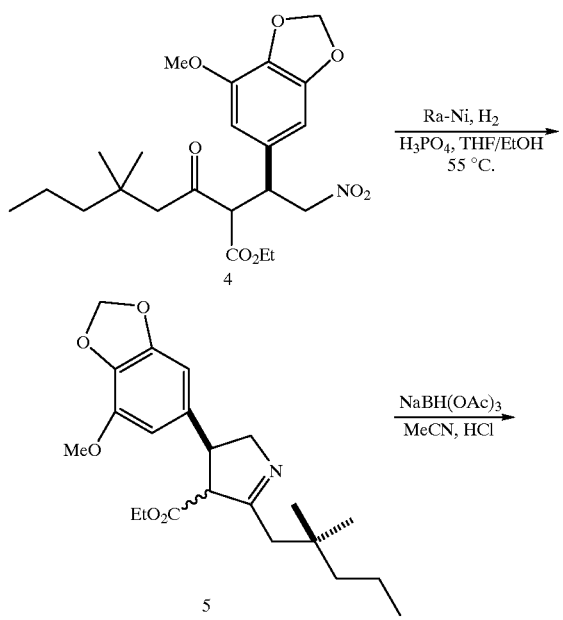

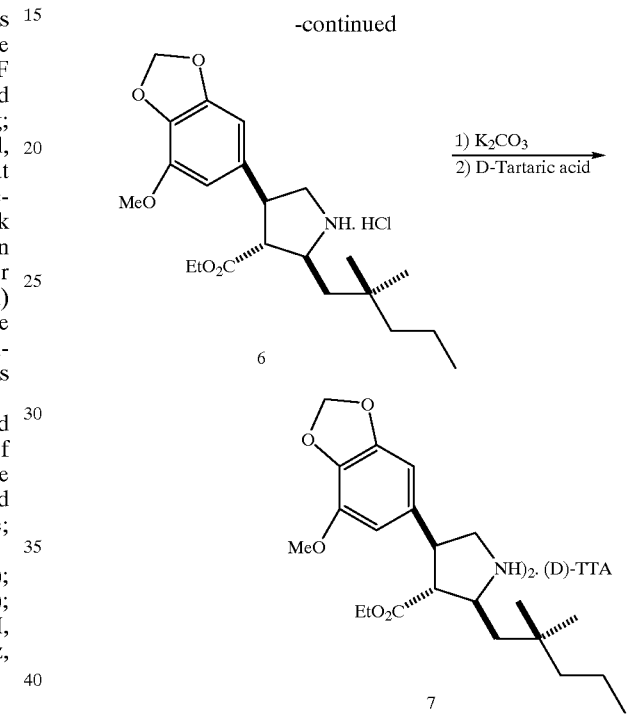

Bis(oxazoline) 3. 100 mL of THF was added to bis (oxazoline) 2 (16.5 g, 50 mmol, 1.0 equiv.). NaH (60% in mineral oil, 10.0 g, 250 mmol, 5.0 equiv.) was added, followed by 1,2-dibromoethane (14.1 g, 75 mmol, 1.5 equiv.). The reaction was heated to 40° C. for 10 min., then cooled to 0° C. Saturated aqueous NH4Cl (20 mL) was added carefully, then the THF was removed in vacuo. 50 mL of water and 50 mL of hexanes were added, and stirred 30 min. The resulting suspension was filtered, and the product was washed sequentially with 50 mL of water and 50 mL of hexanes to provide 17.3 g (97%) Bis(oxazoline) 3.

3: $^1$H NMR (300 MHz/CDCl₃) δ7.45 (m, 2H, Ar—H); 7.27–7.19 (m, 6H, Ar—H); 5.52 (d, J=7.7 Hz, 2H, N—CH); 5.33 (m, 2H, O—CH); 3.39 (dd, J=7.0, 18.0 Hz, 2H, Ar—CHH); 3.20 (dd, J=1.8, 18.0 Hz, 2H, Ar—CHH); 1.36 (m, 2H, —CHH—CHH—); 1.27 (m, 2H, —CHH—CHH—).

EXAMPLE 2

Preparation of β-Keto-ester

2a) Synthesis of Ethyl 3,3-Dimethylhexnoate

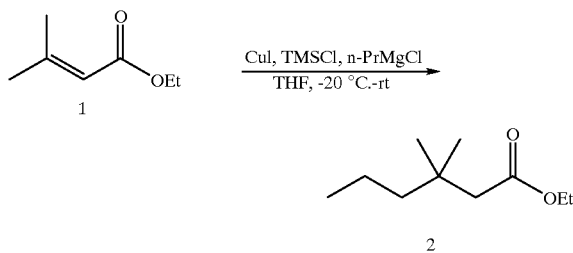

Under N$_2$, ethyl 3,3-dimethylacrylate (226 grams (g), 1.76 moles (mol)), tetrahydrofuran (THF) (2 liters (L)), chlorotrimethylsilane (335 milliliters (mL), 2.64 mol) and copper(I) iodide (33.5 g, 0.18 mol) were added to a 5 L three-necked flask equipped with a 1-L additional funnel, a thermometer and an over-head stirrer, at room temperature. The mixture was stirred and cooled down to −20° C. The addition funnel was filled with n-propylmagnesium chloride (2.0 M in ether, 0.66 L+0.66 L, 2.64 mol) and this solution was slowly added to the flask over 2 hours while maintaining the temperature at less than −10° C. During the addition, the solution in the flask became gray, green, blue, and finally dark. After the addition was finished, the cooling bath was removed and the reaction mixture was continually stirred at ambient temperature for about 3 hours. The reaction was quenched by adding ammonium chloride [141 g in HCl (5%, 1 L) and ice water(0.5 L)]. The dark blue mixture was stirred vigorously for 10 hours. The organic layer was decanted; the aqueous solution was extracted with methyl tert-butyl ether (MTBE) (3×500 mL). The combined organic solution was washed with H$_3$PO$_4$ (30%,w 2×300 mL), brine (2×500 mL) and was then concentrated in vacuum on rotavapor at room temperature. The reaction gave 284 g of ethyl 3,3-dimethylhexnoate. (yield 93.8%). $^1$H NMR (CDCl$_3$/300 MHz): δ4.15(q, 2H, J=6.0 Hz), 2.12(s, 2H), 1.32–1.22(m, 7H), 0.98(s, 6H), 0.8(t, 3H, J=5.8 Hz) ppm.

2b) Synthesis of 3,3-Dimethylhexnoic Acid

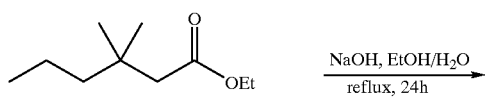

Ethyl 3,3-dimethylhexanoate (from above) (280 g, 1.63 mol), ethyl alcohol (400 mL) and aqueous sodium hydroxide solution (98 g, 2.45 mol, in 200 mL of water) were added to a 2-L round flask equipped with a stirring bar. The solution was then heated to refluxing temperature and stirred for 24 hours. After the reaction was finished, most of the solvents were removed by evaporation. The residue was taken up in 500 mL of ice water. It was then acidified to pH=3 with HCl (10%, w. ~500 mL). The mixture was extracted with MTBE (3×500 mL). The combined MTBE extracts were washed with brine (2×50 mL) and dried over magnesium sulfate (~40 g). The drying reagent was filtered and the MTBE was removed to give 223 g of 3,3-dimethylhexanoic acid (yield 95.1%). $^1$H NMR (CDCl$_3$/300 MHz): δ2.25(s, 2H), 1.32–1.26(m, 4H), 1.02(s, 6H), 0.90(m, 3H) ppm; $^{13}$C NMR (CDCl$_3$/300 MHz): δ179.0, 45.8, 44.6, 33.2, 27.2, 17.5, 14.8 ppm; MS 162 (M$^+$+NH$_4^+$).

2c) Synthesis of Ethyl 5,5-Dimethyl-3-oxo-octanoate

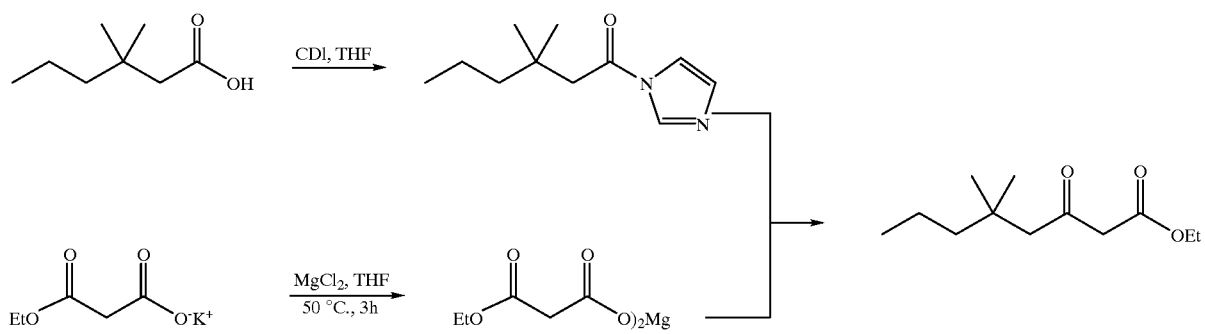

Under N$_2$, 1,1'-Carbonyldiimidazole (294 g, 1.82 mol) and THF (1000 mL) was slowly added to 3,3-dimethylhexanoic acid (238 g, 1.65 mol in 200 mL of THF), to a 2 L 3-necked flask. After the addition was completed, the solution was stirred at ambient temperature for 3 hours. Ethyl malonate potassium salt (281 g, 1.65 mol), THF (1500 mL) and magnesium chloride (157 g, 1.65 mol) were added under N$_2$ to a flask equipped with an over-head stirrer. The mixture was stirred at 50° C. for 3 hours. It was then cooled down to room temperature and above acid imidazolide solution was added. The resultant slurry was stirred for 18 hours. H$_3$PO$_4$ (30%, 1.5 L) was added and the mixture was stirred for 1 hour. The aqueous layer was separated and extracted with MTBE (3×700 mL). The combined organic layer was washed with K$_2$CO$_3$ (25%, 2×500 mL) and brine (1000 mL) and dried over magnesium sulfate (~40 g). The drying reagent was filtered and solvent was removed to give 250 g of ethyl 5,5-dimethyl-3-oxo-octanoate (yield 71%).

1H NMP (CDCl$_3$/300 MHz) δ4.91(s, 0.5H, β-enol ester), 4.18(m,2H), 3.40(s, 1.5H, β-keto ester), 2.42(s, 1.5H, β-keto ester), 2.05(d, J=2 Hz, 0.5H, β-enol ester), 1.36–1.16(m, 7H), 0.94(s, 3H), 0.88(s, 3H), 0.85(m, 3H)ppm.

EXAMPLE 3
Preparation of Nitrostyrene

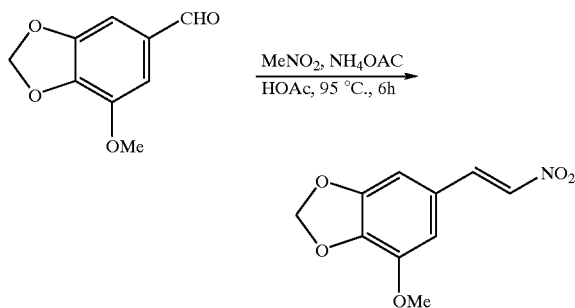

Under $N_2$, 3-Methoxy-4,5-methylenedioxybenzaldehyde (928 g, 97%, w., 5 mol), Acetic acid (2.5 L), followed by ammonium acetate (664 g, 8.5 mol) and HOAc (1 L) were added to a 22-L 4-necked flask equipped with a an overhead stirrer, a thermometer and a refluxing condenser. The mixture was stirred at room temperature for 10 minutes. Nitromethane (1350 mL, 25 mol) and acetic acid (1 L) were subsequently added. The mixture was heated and stirred at 95° C. for 6 hours. The reaction was monitored with HPLC [HPLC conditions: Zorbax Rx-C8 (25 cm×4.6 mm); column temperature 35° C.; gradient elution from 5:95 to 90:10-acetonitrile:water (0.1% phosphoric acid) in 15 minutes; flow-1.5 mL/min.; UV detection at 230 nm. Retention time: 3-Methoxy-4,5-methylenedioxybenzaldehyde-9.7 min.; 4-Methoxy-6(2-nitrovinyl)-1,3-Benzodioxole-11.8 min.]. After the reaction was completed, the mixture was cooled down to room temperature and filtered. The yellow solid was washed with acetic acid (2×500 mL) and water (2×1000 mL) and the product was dried under vacuum for 3 days to give 997 g of product. (yield 89%) $^1$H NMR(CDCl$_3$/300 MHz) 7.90(d, J=15.0 Hz, 1H), 7.48(d, J=15.0 Hz, 1H), 6.74(m, 2H), 6.08(s, 2H), 3.95(s, 3H) ppm.

EXAMPLE 4
Production of Nitroketone

A dry 250-mL round bottom flask equipped with a magnetic stirrer was charged with Magnesium trifluoromethane-sulfonate [Mg(OTf)$_2$], (80 wt. % by KF; 323 mg; 0.80 mmol; 0.040 equiv.) and ligand 3 (392 mg; 1.1 mmol; 0.055 equiv.). 20 mL of CHCl$_3$ was added, and the mixture was stirred for 1.25 h. 80 mL of CHCl$_3$ was added, followed by 4 g of powdered 4 A molecular sieves. The resulting mixture was stirred for 1.5 h. Nitrostyrene 1 (4.46 g; 20 mmol; 1 equiv.) was added in one portion, followed by ketoester 2 (5.6 mL; 5.1 g; 24 mmol; 1.2 equiv.). N-Methylmorpholine (0.11 mL; 1.0 mmol; 0.05 equiv.) was added, and the reaction was fitted with a distillation column and placed in an oil bath at 35° C. After 18 h, the reaction was removed from the bath and concentrated to 15–20 mL. 100 mL of MTBE was added and reconcentrated to ~15 mL.

100 mL of MTBE was added and a gray residual solid containing mostly molecular sieves was filtered out. The solid was washed with 10 mL of MTBE. The resulting dark brown organic solution was collected and washed first with 20 mL of 5% aq. H$_3$PO$_4$ then with 20 mL of H$_2$O. The organic layer was concentrated again to ~20 mL.

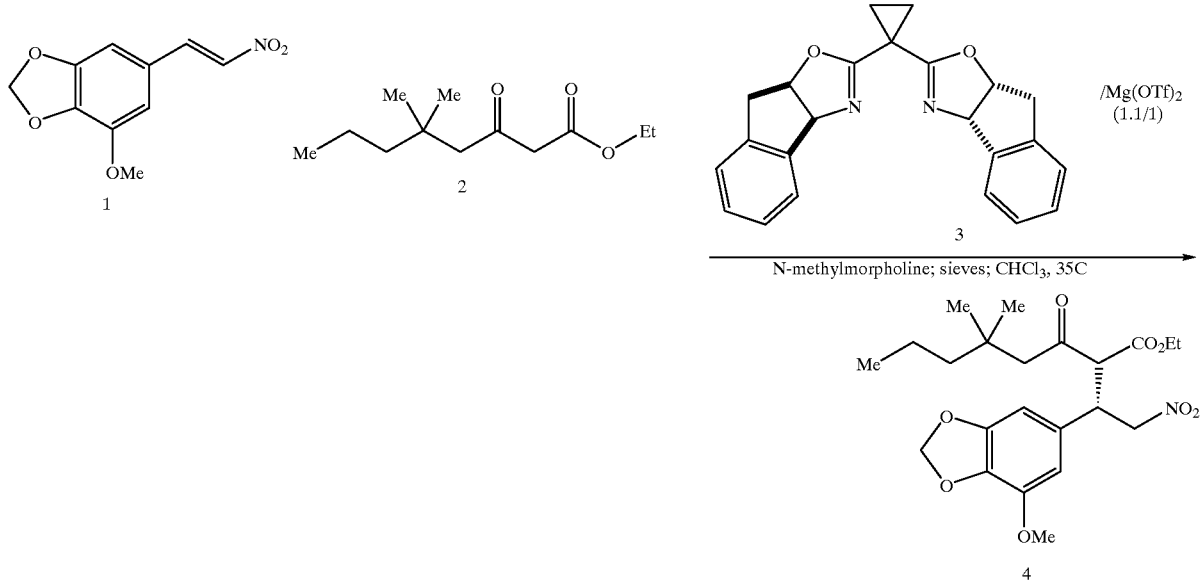

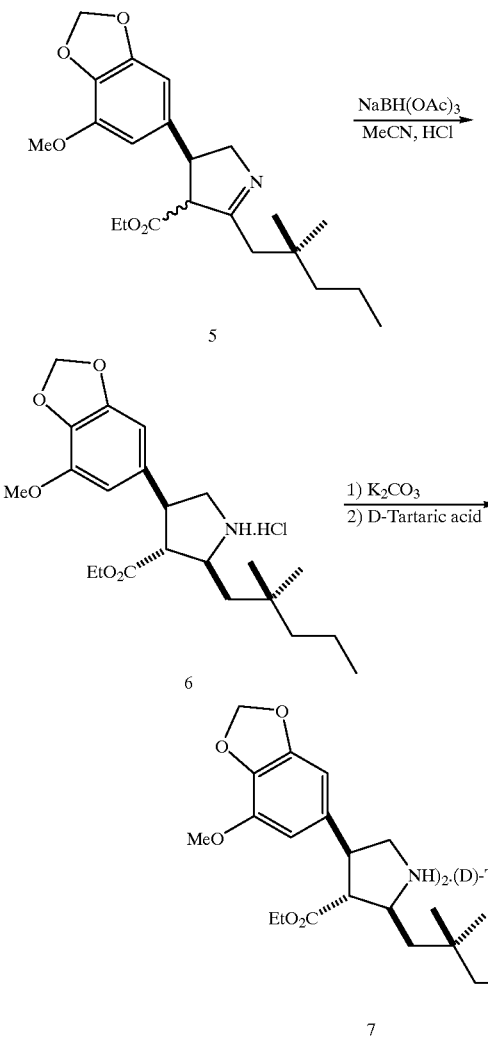

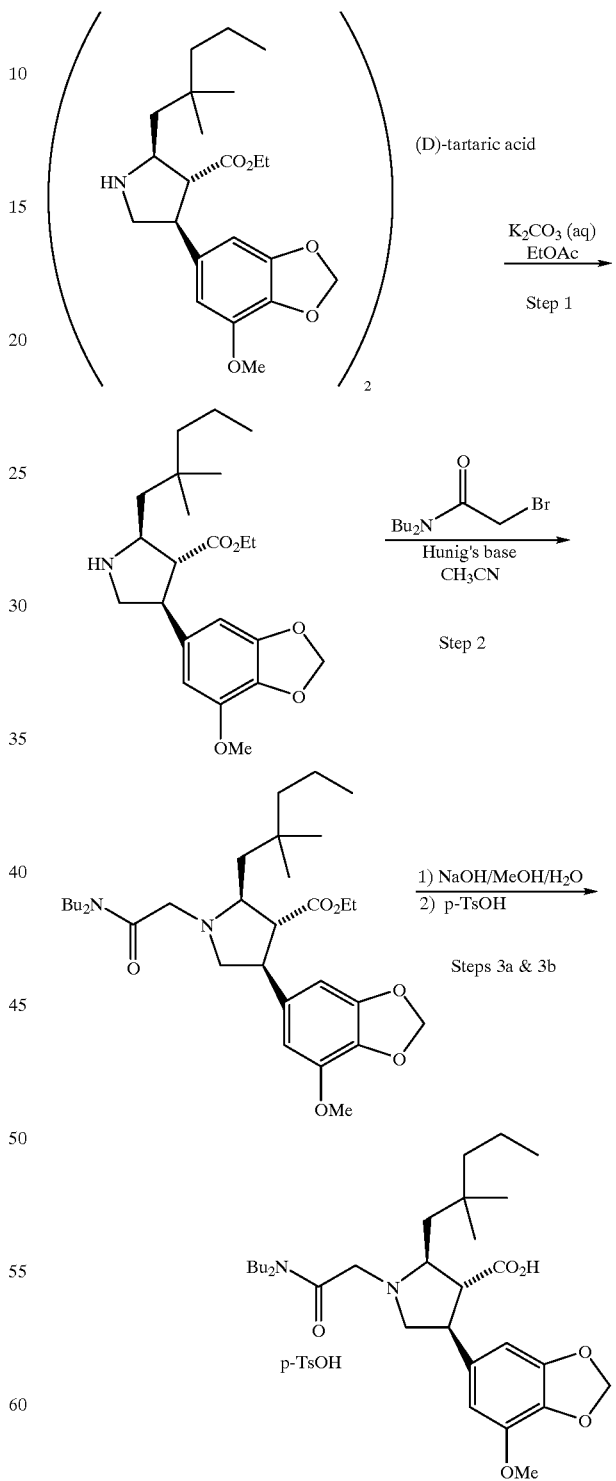

Hydrogenation: The crude nitroketone 4 was transferred to a 50 mL volumetric flask and diluted to 50 mL with THF (0.15 g/mL) for the next step. To a flask containing 13.7 mL of the above THF solution (2.05 g of 4, 4.68 mmol) was added 1.3 mL of THF and 2.0 mL of EtOH. The mixture was transferred to a high pressure vessel. 3.3 g of Ra—Ni (washed twice with $H_2O$) and 85% $H_3PO_4$ (0.2 mL) were then added. The resultant mixture was hydrogenated under 4 atmospheres of hydrogen at 55° C. When hydrogen uptake ceased the reaction was stopped and Ra—Ni was filtered out. Solvents were removed in vacuum (imine 5 is $O_2$ sensitive, air should be avoided) for the next step.

Reduction: Under $N_2$, 20 mL of MeCN was added to the above residue followed by $NaBH(OAc)_3$ (11.7 mmol, 2.5 eq., freshly prepared from $NaBH_4$ and HOAc in 5 mL of MeCN). HCl (concentrated) was slowly added to the brown mixture until pH =2–3. The reaction mixture was stirred at ambient temperature for 4 hours.

Crystallization: Saturated $K_2CO_3$ (~15%, w) (10 mL) was added to the above mixture and stirred at rt for 0.5 h. Solvents was then removed in vacuum. The free amine was then extracted with 50 mL of EtOAc. The organic solution was washed twice with 10 mL of $H_2O$. The combined organic layers were concentrated. (D)-Tartaric acid (0.30 g, 2.0 mmol), in 6 mL MeOH was then added to the brown solution. The mixture was heated to 55–60° C. and then slowly cooled to 24° C. and stirred for 2 days. A solid was filtered off. After drying, the salt 7 weighed 1.38 g (70% yield).

EXAMPLE 5

This briefly describes the procedures used to prepare (2S, 3R, 4S)-2-3-Fluoro-4-methoxyphenyl)-4-(1,3-benzodioxol-5-yl)-1-(2-(N-propyl-N-pentanesulfonyl)ethyl)pyrrolidine-3-carboxylic acid (tosylate salt) from the (D)-tartaric acid salt used to resolve the pyrollidine.

Step 1; Free Base

A mixture of tartrate salt (288.5 g, 309 mmole), 10% potassium carbonate solution (1.29 kg, 933 mmole), and ethyl acetate (3.0 L) were vigorously stirred a rt for 2 hours at which time all solids had dissolved. The layers were separated and the organic portion was concentrated in vacuo to approximately half volume. HPLC weight assay versus a standard showed 241.3 g amine in solution (theory=>241.9 g). The remaining solvent was evaporated in vacuo to leave 257.4 g brown oil.

Step 2; Alkylation

The free based amine (241.3 g by assay, 616 mmole) was dissolved in acetonitrile (700 mL) and was treated with α-bromo-N,N-dibutylacetamide (184 g, 647 mmole) and diisopropylethylamine (87.5 g, 677 mmole). The mixture was heated to ca. 65° to 70° C. briefly and then allowed to cool to ambient temperature. The bulk of the solvent was removed in vacuo leaving 563 g brown slurry.

Step 3a; Saponification

The crude product from above (563 g, 616 mmole) was dissolved in methanol (1.0 L) and then a solution of NaOH (98.2 g, 2.46 mole) in water (500 mL) was added. The mixture was stirred at 65° C. for 2 hours. The reaction was allowed to cool to rt, and assayed by HPLC versus a standard for 327.9 g A-216546. The bulk of the methanol was removed in vacuo.

Step 3b; Salt Formation

The mixture was partitioned between ethyl acetate (1.5 L) and water (0.5 L). The organic layer was treated with p-toluenesulfonic acid monohydrate (260 g, 1.37 mole) and the resulting solution was then washed with water (0.5 L). The organic phase was separated and concentrated in vacuo. The resultant oil was dissolved in methyl t-butyl ether (1.0 L), seeded with crystalline A-216546.47, and stirred at rt. The solids were collected by filtration, rinsed with MTBE, and dried to give 252. (2S, 3R, 4S)-2-3-Fluoro-4-methoxyphenyl)-4-(1,3-benzodioxol-5-yl)-1-(2-N-propyl-N-pentanesulfonyl)ethyl)pyrrolidine-3-carboxylic acid (tosylate salt).

We claim:

1. A stereoselective process of producing a nitromethyl compound having Formula Va or Vb

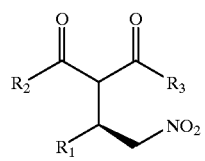

Va

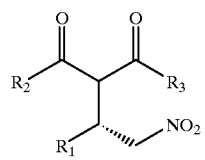

Vb by reacting a nitroolefin having formula III

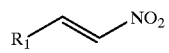

III with a beta dicarbonyl compound having formula IV

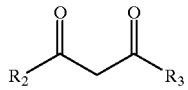

IV wherein R1=aryl, alkyl or arylalkyl, R2 and R3 are independently selected from alkoxy, alkyl, arylalkyl, or aryl, in the presence of a catalyst complex and a base, said catalyst complex comprising a ligand and a metal complex, wherein the ligand has the formula I

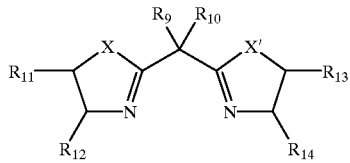

I wherein
R9 and R10 are independently selected from the group consisting of hydrogen, alkyl, aryl, and arylalkyl, or R9 and R10 taken together can form a 3, 4, 5, or 6-membered cycloalkyl ring or a bicyclic ring;
X and X' are independently selected from the group consisting of oxygen, sulfur, and nitrogen;
R11 or R12 may be independently selected from the group consisting of hydrogen, alkyl, arylalkyl, and aryl, or R11 and R12 taken together with the ring to which they are attached may form a bicyclic or tricyclic fused ring; and R13 or R14 may be independently selected from the group consisting of hydrogen, alkyl, arylalkyl, and aryl, or R13 and R14 taken together with the ring to which they are attached may form a bicyclic or tricyclic fused ring; or the ligand can have the formula II,

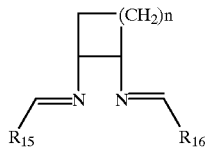

II wherein n is 1–3, and R15 and R16 are independently selected from the group consisting of alkyl, aryl, and arylalkyl.

2. The process of claim 1 wherein said metal complex is selected from the group consisting of magnesium trifluoromethanesulfonate, magnesium perchlorate, copper trifluoromethanesulfonate, zinc trifluoromethanesulfonate, lanthanum trifluoromethanesulfonate, nickel trfuoromethanesulfonate, magnesium bromide, copper bromide, zinc bromide, nickel bromide, magnesium iodide, copper iodide, zinc iodide, nickel iodide, magnesium acetylacetonate, copper acetylacetonate, zinc acetylacetonate, and nickel acetylacetonate.

3. The process of claim 2 wherein said metal complex is magnesium trifluoromethanesulfonate.

4. The process of claim 1 wherein said base is selected from the group consisting of triethylamine, diisopropyl ethylamine, 2,6-lutidine, N-methylmorpholine, N-ethylpiperidine, imidiazole, and 5,6 dimethylbenzimidazole.

5. The process of claim 4 wherein said base is 2,6-lutidine, N-methylmorpholine, and 5,6-dimethylbenzimidazole.

6. The process of claim 1 wherein said metal complex and said ligand are reacted in the presence of a solvent selected from the group consisting of tetrahydrofuran (THF), toluene, methylene chloride, and chloroform.

7. The process of claim 1 for producing a nitroketone compound by reacting a nitrostyrene compound having the formula

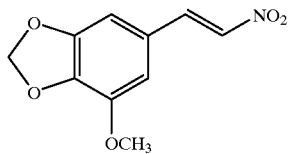

with a dicarbonyl compound having the formula

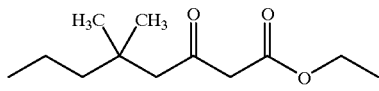

to produce a nitroketone compound having the formula

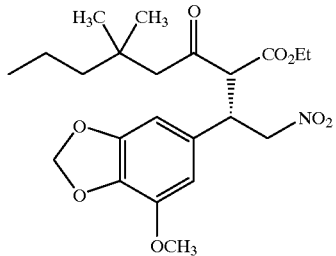

reacting said nitrostyrene and said dicarbonyl in the presence of a catalyst complex and a base.

8. The process of claim 7 wherein said catalyst complex is produced by reacting a ligand with a metal complex, said metal complex is selected from the group consisting of magnesium trifluoromethanesulfonate, magnesium perchlorate, copper trifluoromethanesulfonate, zinc trifluoromethanesulfonate, lanthanum trifluoromethanesulfonate, nickel trifluoromethanesulfonate, magnesium bromide, copper bromide, zinc bromide, nickel bromide, magnesium iodide, copper iodide, zinc iodide, nickel iodide, magnesium acetylacetonate, copper acetylacetonate, zinc acetylacetonate, and nickel acetylacetonate.

9. The process of claim 8 wherein said metal complex is magnesium trifluoromethanesulfonate.

10. The process of claim 7 wherein said base is selected from the group consisting of triethylamine, diisopropyl ethylamine, 2,6-lutidine, N-methylmorpholine, N-ethylpiperidine, imidiazole, and 5,6-dimethylbenzimidazole.

11. The process of claim 10 wherein said base is 2,6-lutidine, N-methylmorpholine, and 5,6-dimethylbenzimidazole.

12. The process of claim 8 wherein said metal complex and said ligand are reacted in the presence of a solvent selected from the group consisting of tetrahydrofuran (THF), toluene, methylene chloride, and chloroform.

* * * * *